United States Patent
Morita

(10) Patent No.: US 11,099,374 B2
(45) Date of Patent: Aug. 24, 2021

(54) ENDOSCOPE

(71) Applicant: OLYMPUS CORPORATION, Hachioji (JP)

(72) Inventor: Akari Morita, Saitama (JP)

(73) Assignee: OLYMPUS CORPORATION, Tokyo (JP)

( * ) Notice: Subject to any disclaimer, the term of this patent is extended or adjusted under 35 U.S.C. 154(b) by 92 days.

(21) Appl. No.: 16/715,387

(22) Filed: Dec. 16, 2019

(65) Prior Publication Data
US 2020/0142177 A1     May 7, 2020

Related U.S. Application Data

(63) Continuation of application No. PCT/JP2018/009756, filed on Mar. 13, 2018.

(30) Foreign Application Priority Data

Jun. 29, 2017 (JP) .............................. JP2017-126907

(51) Int. Cl.
*G02B 23/24* (2006.01)
*A61B 1/00* (2006.01)
(Continued)

(52) U.S. Cl.
CPC ...... *G02B 23/2469* (2013.01); *A61B 1/00096* (2013.01); *A61B 1/07* (2013.01); *G02B 23/243* (2013.01); *G02B 23/26* (2013.01)

(58) Field of Classification Search
CPC .............. G02B 23/2469; G02B 23/243; A61B 1/00096; A61B 1/07
See application file for complete search history.

(56) References Cited

U.S. PATENT DOCUMENTS 4,671,630 A * 6/1987 Takahashi ................ A61B 1/07
  359/389
8,948,560 B1    2/2015 Wach
(Continued)

FOREIGN PATENT DOCUMENTS

EP     1891885 A1    2/2008
EP     8369363 A1    9/2018
(Continued)

OTHER PUBLICATIONS

International Search Report (ISR) dated Jun. 5, 2018 (and English translation thereof) issued in International Application No. PCT/JP2018/009756.

(Continued)

*Primary Examiner* — William N Harris
(74) *Attorney, Agent, or Firm* — Holtz, Holtz & Volek PC

(57) ABSTRACT

An endoscope includes: a light guide fiber having an exit end through which illumination light is emitted; a transparent distal-end element configured to hold the exit end of the light guide fiber and made of a transparent material that allows the illumination light emitted from the exit end to pass therethrough; and an objective optical system inserted through a through-hole provided in the transparent distal-end element, wherein at least a portion of the illumination light enters the objective optical system through a boundary between the transparent distal-end element and the objective optical system, and a refractive index of the transparent material constituting the transparent distal-end element is larger than a refractive index of at least one material in contact with an inner surface of the through-hole.

17 Claims, 5 Drawing Sheets

(51) Int. Cl.
*A61B 1/07* (2006.01)
*G02B 23/26* (2006.01)

(56) References Cited

U.S. PATENT DOCUMENTS

| | | | |
|---|---|---|---|
| 9,838,576 B2* | 12/2017 | Haraguchi | H04N 5/2253 |
| 2004/0199052 A1 | 10/2004 | Banik et al. | |
| 2005/0119527 A1 | 6/2005 | Banik et al. | |
| 2005/0131279 A1 | 6/2005 | Boulais et al. | |
| 2005/0154262 A1 | 7/2005 | Banik et al. | |
| 2005/0197536 A1 | 9/2005 | Banik et al. | |
| 2005/0222499 A1 | 10/2005 | Banik et al. | |
| 2005/0245789 A1 | 11/2005 | Smith et al. | |
| 2008/0045798 A1 | 2/2008 | Fukuhori | |
| 2008/0242935 A1 | 10/2008 | Inoue | |
| 2009/0281385 A1* | 11/2009 | Hatoma | A61B 1/07 600/114 |
| 2010/0286475 A1* | 11/2010 | Robertson | A61B 1/00096 600/104 |
| 2014/0160571 A1 | 6/2014 | Miyazaki et al. | |
| 2016/0100750 A1 | 4/2016 | Furuta | |
| 2016/0106306 A1 | 4/2016 | Furuta | |
| 2017/0035282 A1* | 2/2017 | Kaneko | A61B 1/06 |
| 2017/0059848 A1* | 3/2017 | Haraguchi | G02B 23/2469 |
| 2018/0303325 A1 | 10/2018 | Fujimori | |

FOREIGN PATENT DOCUMENTS

| | | |
|---|---|---|
| JP | S5734826 A | 2/1982 |
| JP | S63136015 A | 6/1988 |
| JP | H03264037 A | 11/1991 |
| JP | H07294828 A | 11/1995 |
| JP | H09197292 A | 7/1997 |
| JP | H09236758 A | 9/1997 |
| JP | H09285440 A | 11/1997 |
| JP | H105171 A | 1/1998 |
| JP | H11249030 A | 9/1999 |
| JP | 2002065587 A | 3/2002 |
| JP | 2004041457 A | 2/2004 |
| JP | 2004049793 A | 2/2004 |
| JP | 2004267255 A | 9/2004 |
| JP | 2006239185 A | 9/2006 |
| JP | 2006521882 A | 9/2006 |
| JP | 2008043626 A | 2/2008 |
| JP | 2008514381 A | 5/2008 |
| JP | 2008237790 A | 10/2008 |
| JP | 2009207529 A | 9/2009 |
| JP | 2009207578 A | 9/2009 |
| JP | 2011200428 A | 10/2011 |
| JP | 2013202082 A | 10/2013 |
| JP | 2013202347 A | 10/2013 |
| JP | 2014014611 A | 1/2014 |
| JP | 2015016020 A | 1/2015 |
| JP | 2015016022 A | 1/2015 |
| JP | 5874007 B2 | 3/2016 |
| JP | 2016150215 A | 8/2016 |
| WO | 2004086957 A2 | 10/2004 |
| WO | 2006039646 A2 | 4/2006 |
| WO | 2017072847 A1 | 5/2017 |

OTHER PUBLICATIONS

Written Opinion (WO) dated Jun. 5, 2018 issued in International Application No. PCT/JP2018/009756.

* cited by examiner

ENDOSCOPE

CROSS-REFERENCE TO RELATED APPLICATIONS

This is a continuation of International Application PCT/JP2018/009756, with an international filing date of May 13, 2018, which is hereby incorporated by reference herein in its entirety. This application claims the benefit of Japanese Patent Application No. 2017-126907, the content of which is incorporated herein by reference.

TECHNICAL FIELD

The present invention relates to endoscopes.

BACKGROUND ART

A known endoscope includes an insertion part that holds a light guide fiber, and a tubular transparent distal-end element that is made of a transparent material capable of allowing illumination light emitted from the light guide fiber to pass therethrough. An objective optical system is disposed so as to be inserted through a central hole in the transparent distal-end element (for example, see Patent Literature 1).

In the endoscope in Patent Literature 1, a lens group constituting the objective optical system is assembled in a state surrounded by a tubular frame, and the objective optical system and the transparent distal-end element are completely partitioned in the radial direction by the frame. Hence, the occurrence of flare due to the illumination light emitted from the light guide fiber entering the objective optical system through the transparent distal-end element is suppressed.

CITATION LIST

Patent Literature

{PTL 1} Japanese Unexamined Patent Application Publication No. 2009-207529

SUMMARY OF INVENTION

An aspect of the present invention is directed to an endoscope including: a light guide fiber having an exit end through which illumination light is emitted; a transparent distal-end element configured to hold the exit end of the light guide fiber and made of a transparent material that allows the illumination light emitted from the exit end to pass therethrough; and an objective optical system inserted through a through-hole provided in the transparent distal-end element, wherein at least a portion of the illumination light enters the objective optical system through a boundary between the transparent distal-end element and the objective optical system, and a refractive index of the transparent material constituting the transparent distal-end element is larger than a refractive index of at least one material in contact with an inner surface of the through-hole.

Another aspect of the present invention is directed to an endoscope including: a light guide fiber having an exit end through which illumination light is emitted; a transparent distal-end element configured to hold the exit end of the light guide fiber and made of a transparent material that allows the illumination light emitted from the exit end to pass therethrough; and an objective optical system inserted through a through-hole provided in the transparent distal-end element, wherein a refractive index of the transparent material constituting the transparent distal-end element is larger than a refractive index of at least one material in contact with an inner surface of the through-hole, and an outer peripheral surface at a distal end portion of the objective optical system and an inner surface at the distal end portion of the through-hole in the transparent distal-end element have inclined surfaces that are gradually tapered toward distal ends thereof.

Another aspect of the present invention is directed to an endoscope including: a light guide fiber having an exit end through which illumination light is emitted; a transparent distal-end element configured to hold the exit end of the light guide fiber and made of a transparent material that allows the illumination light emitted from the exit end to pass therethrough; and an objective optical system inserted through a through-hole provided in the transparent distal-end element, wherein a refractive index of the transparent material constituting the transparent distal-end element is larger than a refractive index of at least one material in contact with an inner surface of the through-hole, the objective optical system includes a plurality of resin layers laminated in an optical axis direction, outer peripheral surfaces of the plurality of resin layers are in contact with the inner surface of the through-hole, and the refractive indices of the plurality of resin layers increase toward a distal end.

DESCRIPTION OF EMBODIMENTS

An endoscope 1 according to an embodiment of the present invention will be described below with reference to the drawings.

Figure 1:
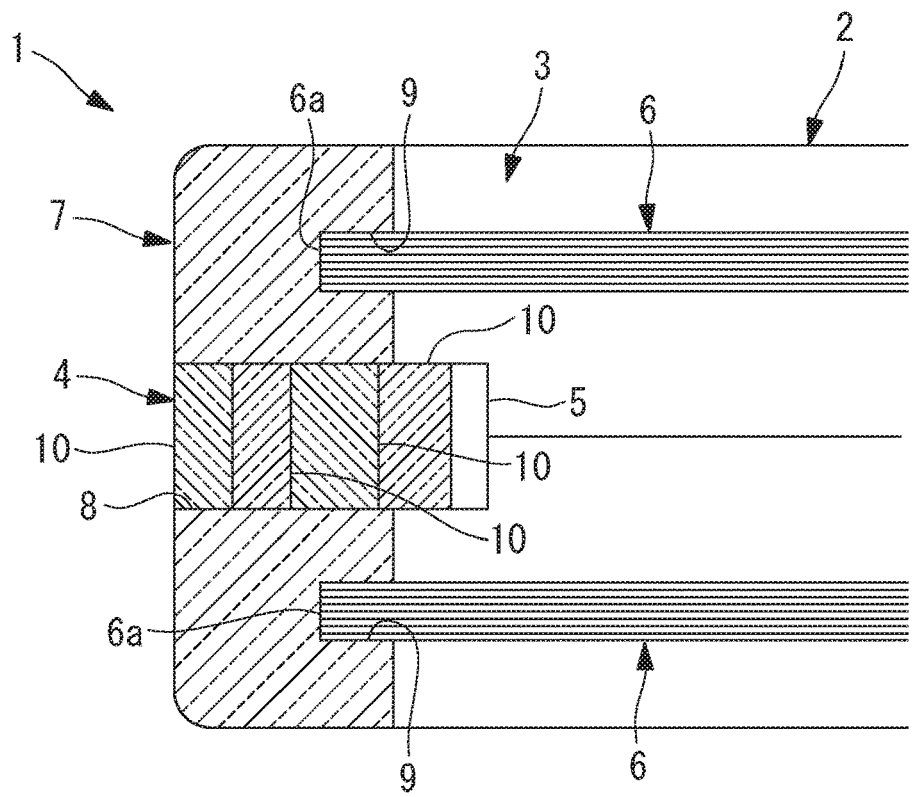
FIG. 1 is a partial vertical sectional view of a distal end portion of an endoscope according to an embodiment of the present invention.

As shown in FIG. 1, the endoscope 1 according to this embodiment includes an illumination optical system 3 provided at the distal end of an elongated insertion part 2 to radiate illumination light onto a subject, an objective optical system 4 that collects observation light returning from the subject, and an image capturing element 5 that captures an image of the observation light collected by the objective optical system 4.

The illumination optical system 3 includes light guide fibers 6 that guide the illumination light emitted from light sources (not shown) disposed at the base end of the insertion part 2 to the distal end of the insertion part 2, and a transparent distal-end element 7 made of a transparent material that allows the illumination light emitted from exit ends 6a at the distal ends of the light guide fibers 6 to pass therethrough.

The transparent distal-end element 7 is formed in a substantially cylindrical shape and has, at the center thereof, a through-hole 8 penetrating in the axial direction and having a square cross section. The transparent material constituting the transparent distal-end element 7 is a resin, such as polysulfone, and has a predetermined refractive index ni.

The transparent distal-end element 7 has, in one end face in the axial direction, a plurality of fitting holes 9 that are spaced apart in the circumferential direction about the axis of the through-hole 8 and into which the exit ends 6a of the light guide fibers 6 are fitted. The fitting holes 9 extend from one end face of the transparent distal-end element 7 in the axial direction to positions at a predetermined depth. By butting the light guide fibers 6 fitted into the fitting holes 9 against the bottom surfaces of the fitting holes 9, the light guide fibers 6 can be supported in a positioned state.

Figure 2:
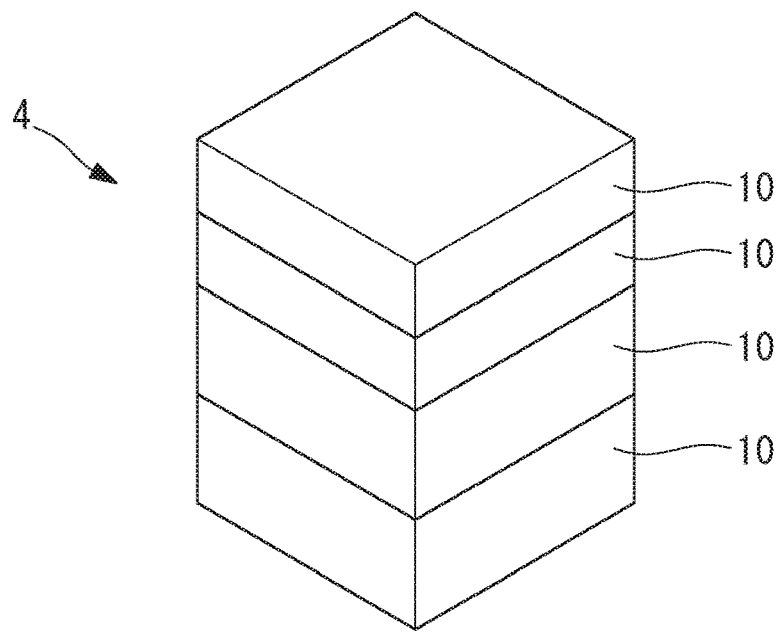
FIG. 2 is a perspective view of an example objective optical system of the endoscope in FIG. 1.

As shown in FIG. 2, the objective optical system 4 is formed in the shape of a substantially square column by laminating resin layers 10 formed of multiple types of resin materials in the axial direction. The cross section of the objective optical system 4 has such dimensions as to perfectly fit in the cross section of the through-hole 8 in the transparent distal-end element 7. The refractive indices nox (x=1, 2, ..., n) of the resin materials of the resin layers 10 constituting the objective optical system 4 satisfy Conditional Expression (1) below:

$$nox \leq ni \tag{1}$$

The objective optical system 4 is produced by cutting, by means of dicing or the like, a substrate that is formed by laminating a large number of resin materials using a thin-film forming technique. The objective optical system 4 is fitted into the through-hole 8 such that the cut surfaces formed when the substrate has been cut by means of dicing or the like are directly brought into contact with the inner surfaces of the through-hole 8 in the transparent distal-end element 7.

In other words, there is no frame between the objective optical system 4 and the transparent distal-end element 7 to block light therebetween.

The image capturing element 5 is a solid-state image capturing element, such as a CCD or CMOS image sensor, and is fixed to an image-plane-side end face, which is the focal position, of the objective optical system 4. Instead of the image capturing element 5, an entrance end of an imaging fiber may be disposed at the end face of the objective optical system 4.

The operation of the thus-configured endoscope 1 according to this embodiment will be described below.

To observe a subject using the endoscope 1 according to this embodiment, the illumination optical system 3 and the objective optical system 4 provided at the distal end of the insertion part 2 are disposed so as to face the subject, and the illumination light emitted from the light source is guided to the distal end of the insertion part 2 through the light guide fibers 6.

The illumination light guided to the distal end of the insertion part 2 through the light guide fibers 6 is emitted forward from the exit ends 6a of the light guide fibers 6, and most of the illumination light passes through the transparent distal-end element 7, which is made of a transparent material, and is radiated onto the subject facing the distal end face of the insertion part 2. The reflection light of the illumination light reflected by the subject and the observation light, such as fluorescence, generated by the subject enter the objective optical system 4 from the distal end face of the objective optical system 4 and are imaged on the image capturing element 5 disposed at the base end of the objective optical system 4. As a result, it is possible to capture, with the image capturing element 5, an image of the observation light coming from the subject and thus to observe the subject.

Figure 3:
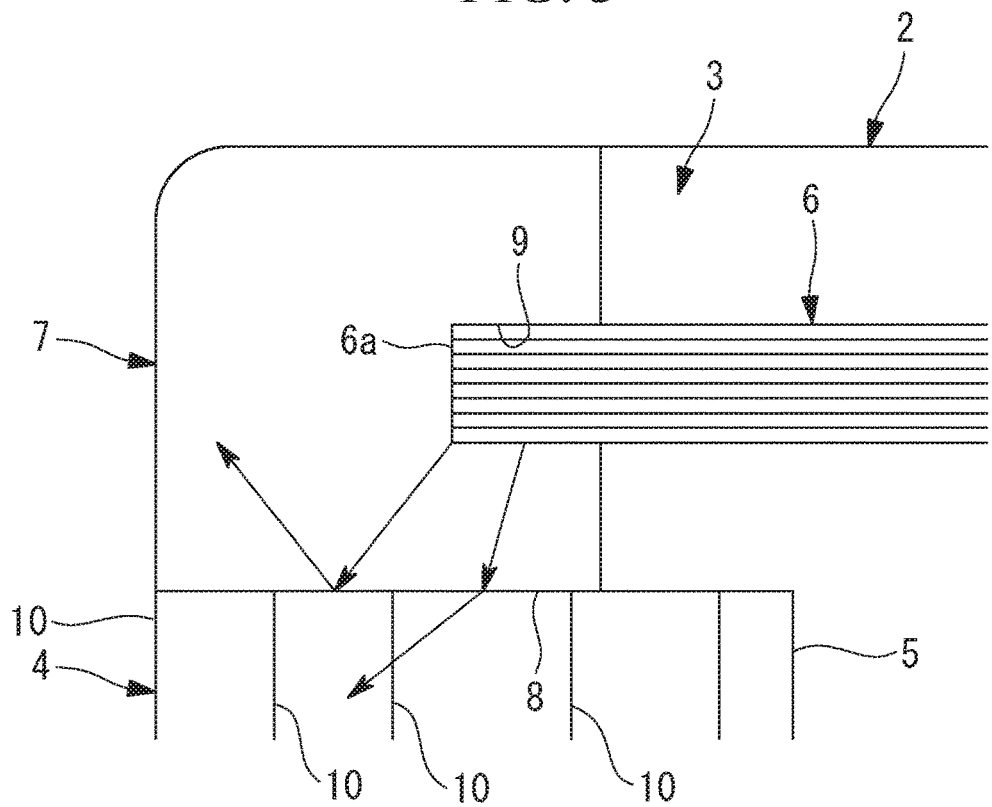
FIG. 3 schematically shows paths of illumination light emitted from a light guide fiber of the endoscope in FIG. 1.

In this case, as shown in FIG. 3, although most of the illumination light emitted from the exit ends 6a of the light guide fibers 6 or the vicinity thereof is emitted obliquely forward, a portion of the illumination light is directed to the through-hole 8 and is incident on the boundary between the transparent distal-end element 7 and the objective optical system 4. Depending on the angle of incidence, a portion of the illumination light incident on the boundary between the transparent distal-end element 7 and the objective optical system 4 so as to be directed obliquely forward is totally reflected at the boundary, and the remaining portion thereof enters the objective optical system 4 through the boundary.

In this embodiment, because the refractive index ni of the transparent material constituting the transparent distal-end element 7 and the refractive indices nox of the resin materials of the resin layers 10 constituting the objective optical system 4 satisfy Conditional Expression (1), the illumination light incident at an angle greater than or equal to the total reflection angle is totally reflected.

The illumination light with a small angle of incidence and not satisfying the total reflection condition enters the objective optical system 4 through the boundary. In this case, because the illumination light is refracted in a further forward direction at the boundary, the illumination light is less likely to be directed to the image capturing element 5 disposed at the base end face of the objective optical system 4.

As described, the endoscope 1 according to this embodiment can be formed simply by directly fitting the square-column-shaped objective optical system 4, which is produced simply by cutting, by means of dicing or the like, a substrate formed by laminating multiple types of resin using a thin-film forming technique, into the through-hole 8 in the transparent distal-end element 7. Hence, there is an advantage in that it is possible to significantly reduce the cost of parts and the assembly cost compared with the conventional endoscope in which a plurality of lenses are set in a frame one-by-one to form the objective optical system 4. There is another advantage in that, by eliminating the frame, it is possible to reduce the outside diameter of the endoscope 1 by an amount corresponding to the thickness of the frame and thus to reduce the diameter of the endoscope 1.

Because the frame is eliminated, the illumination light entering from the transparent distal-end element 7 into the objective optical system 4 is not blocked by the frame. However, by using the difference in refractive index, of the illumination light incident on the boundary between the transparent distal-end element 7 and the objective optical system 4, it is possible to reduce the amount of illumination light passing through the boundary, and also to reduce the illumination light directed to the image capturing element 5 in the illumination light having passed through the boundary. Hence, there is an advantage in that it is possible to effectively prevent the occurrence of flare in the image captured by the image capturing element 5.

Figure 4:
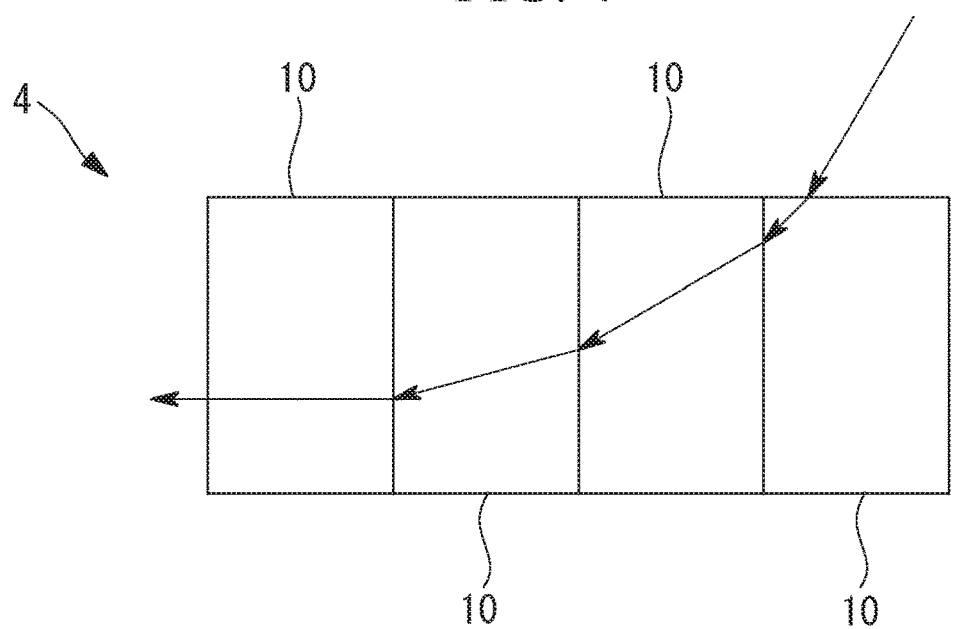
FIG. 4 schematically shows the path of illumination light having entered an objective optical system in a first modification of the endoscope in FIG. 1.

In the endoscope 1 according to this embodiment, it is desirable that the refractive indices nox of the materials of the resin layers 10 constituting the objective optical system 4 be selected so as to increase toward the object side (distal end) in the optical axis direction of the objective optical system 4. With this configuration, as shown in FIG. 4, the illumination light having entered the objective optical system 4 is refracted so as to be directed further to the object side as the illumination light passes through the boundaries between the resin layers 10. This leads to an advantage in that it is possible to reduce the amount of illumination light directed to the image capturing element 5 and thus to more effectively prevent the occurrence of flare.

In this embodiment, although the square-column-shaped objective optical system 4 produced by cutting, by means of dicing, a substrate formed by laminating a plurality of resin layers 10 is used, the optical system is not limited thereto, and a cylindrical objective optical system 4 may also be used. By doing so, it is possible to form the through-hole 8 in the transparent distal-end element 7 so as to have a circular cross section, and thus, the objective optical system 4 and the through-hole 8 can be accurately fitted together.

In this embodiment, although an example configuration has been described in which the refractive index of the transparent material constituting the transparent distal-end element 7 is higher than or equal to the refractive indices of all the resin layers 10 in contact with the inner surface of the through-hole 8, a transparent material having a higher refractive index than at least one (at least a portion) of the materials in contact with the inner surface of the through-hole 8 may be employed. For example, in some cases, depending on the position at which the illumination light enters the objective optical system 4, the illumination light entering the objective optical system 4 does not reach the image capturing face, regardless of the relationship between the refractive indices. In this case, at the position where the illumination light enters the objective optical system 4, the refractive index of the transparent material constituting the transparent distal-end element 7 does not need to be higher than or equal to the refractive index of the resin layer 10. In other words, it is only necessary that the refractive index of the transparent material constituting the transparent distal-end element 7 be higher than or equal to the refractive index of the resin layer 10 at least at the position where there is a path leading the illumination light having entered the objective optical system 4 to the image capturing face.

In the endoscope 1 according to this embodiment, a case where the resin layers 10 constituting the objective optical system 4 are fitted so as to be in direct contact with the inner surface of the through-hole 8 in the transparent distal-end element 7 has been described. Instead, a desired filler may be disposed between the outer peripheral surface of the objective optical system 4 and the inner surface of the through-hole 8 to eliminate a gap therebetween. The filler may be an adhesive. With this configuration, it is possible to reliably fix the objective optical system 4 to the transparent distal-end element 7.

When a filler is disposed between the outer peripheral surface of the objective optical system 4 and the inner surface of the through-hole 8, a filler having a smaller refractive index no than the refractive index ni of the transparent distal-end element 7 is selected. In this case, the refractive indices nox of the resin layers 10 constituting the objective optical system 4 are not limited to those smaller than the refractive index ni of the transparent distal-end element 7. Hence, the degree of freedom in selecting the material can be increased.

Table 1 shows examples of the refractive index ni of the transparent distal-end element 7 and the refractive index no of the material in contact with the inner surface of the through-hole 8.

TABLE 1

| SUBSTANCE IN CONTACT WITH INNER SURFACE OF THROUGH-HOLE | RESIN LAYER P1 | RESIN LAYER P2 | GLASS | AIR | ADHESIVE |
|---|---|---|---|---|---|
| no | 1.546 | 1.532 | 1.497 | 1 | 1.505 |
| TRANSPARENT DISTAL-END ELEMENT | | | POLYSULFONE | | |
| ni | | | 1.635 | | |

According to Table 1, Conditional Expression (1) is satisfied in all the combinations shown in Table 1.

Figure 5:
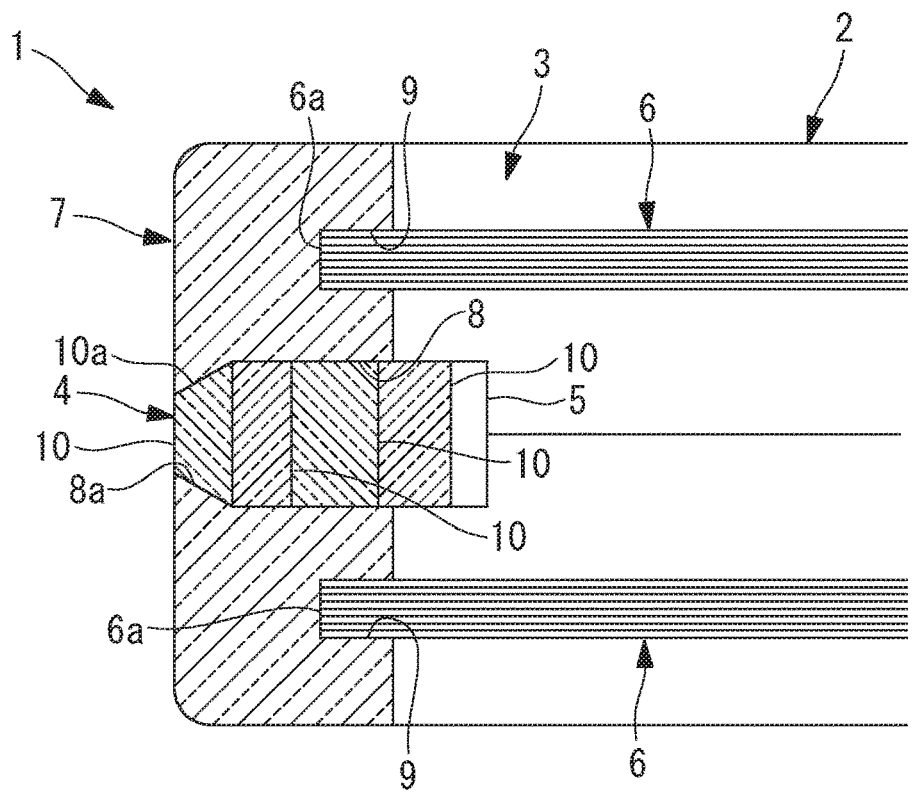
FIG. 5 is a partial vertical sectional view of a distal end portion, showing a second modification of the endoscope in FIG. 1.

Although the objective optical system 4 has a columnar shape having a uniform cross section in this embodiment, instead, as shown in FIG. 5, the objective optical system 4 may have inclined surfaces 10a tapered toward the distal end face (object-side face) on the entire circumference around the optical axis. Then, the through-hole 8 in the transparent distal-end element 7 also has inclined surfaces 8a to be brought into tight contact with the inclined surfaces 10a of the objective optical system 4.

Figure 6:
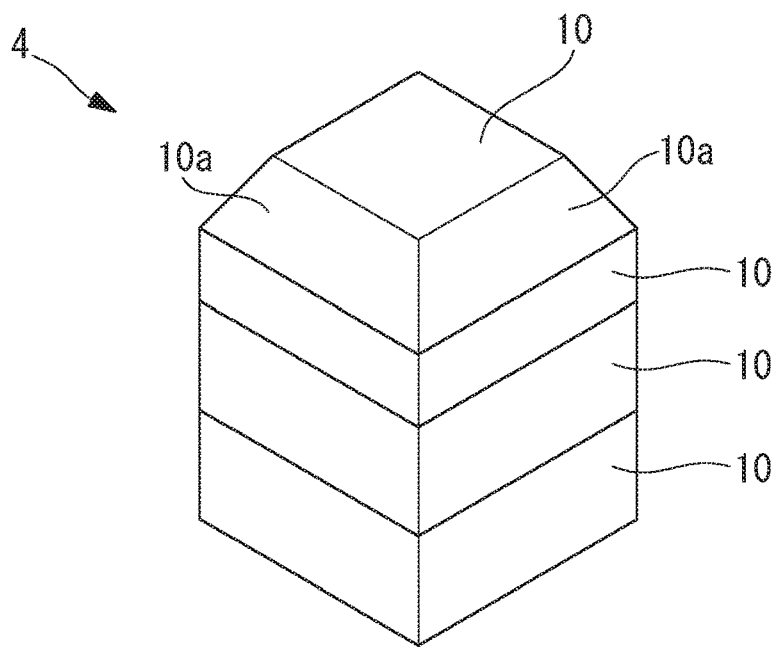
FIG. 6 is a perspective view of an example objective optical system of the endoscope in FIG. 5.
Figure 7:
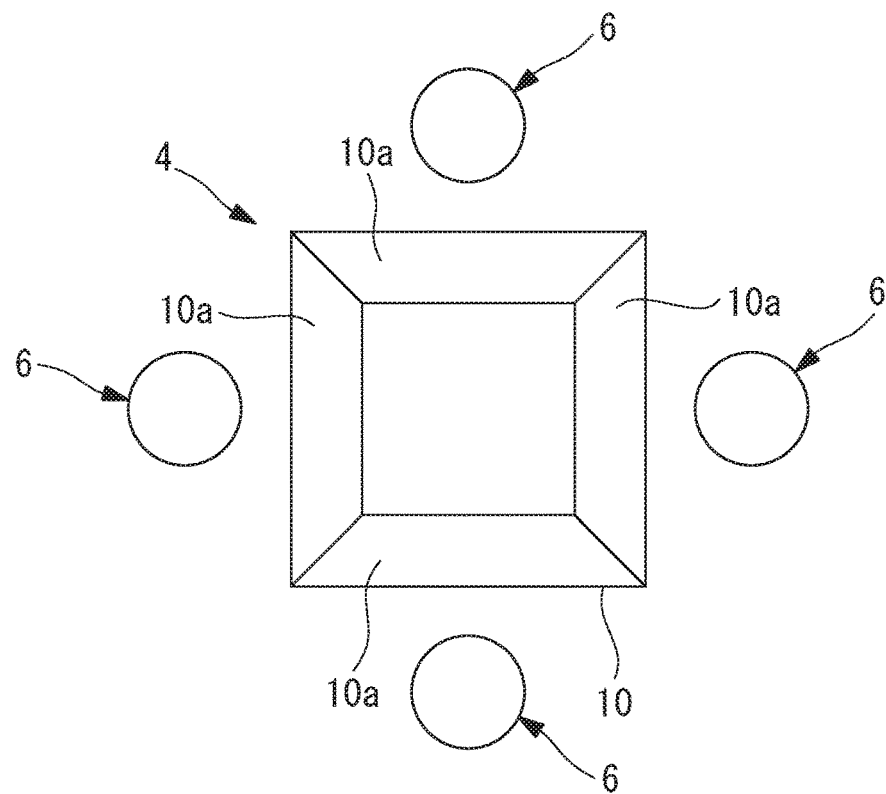
FIG. 7 is a front view showing an example arrangement of the objective optical system in FIG. 6 and light guide fibers.

When the objective optical system 4 is formed in a square-column shape, the inclined surfaces 10a are provided on four side surfaces, as shown in FIG. 6. Hence, it is desirable that the inclined surfaces 10a and the fitting holes 9, to which the exit ends 6a of the light guide fibers 6 are fixed, be disposed at positions corresponding to each other, as shown in FIG. 7. The number of light guide fibers 6 may be any number.

Figure 8:
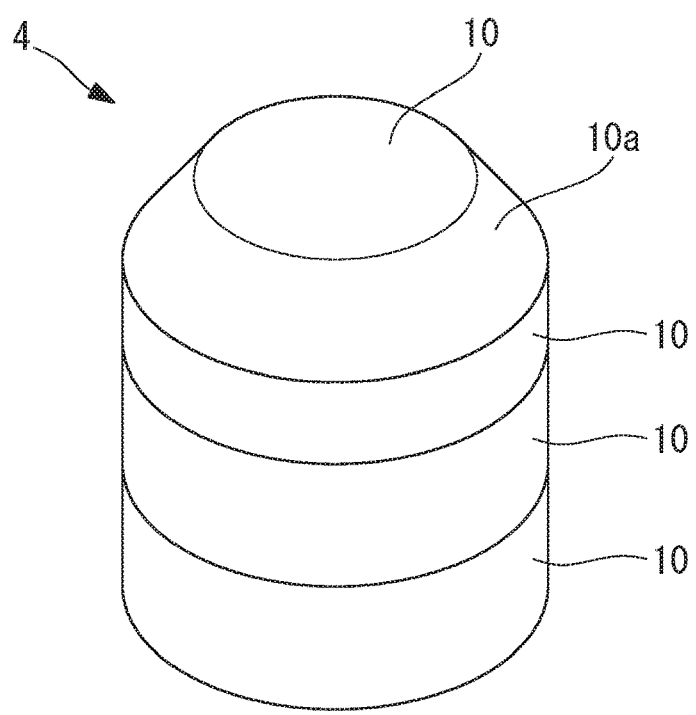
FIG. 8 is a perspective view of a modification of the objective optical system in FIG. 6.

On the other hand, when the objective optical system 4 is cylindrical, as shown in FIG. 8, the fitting holes 9 may be disposed at any positions in the circumferential direction, on the radially outer side of the through-hole 8.

With this configuration, the angle of incidence of the illumination light emitted from the exit ends 6a of the light guide fibers 6 onto the boundary between the transparent distal-end element 7 and the objective optical system 4 can be made larger than that at positions other than the inclined surface 10a. As a result, it is possible to increase the amount of illumination light totally reflected at the boundary and thus to reduce the amount of illumination light entering the objective optical system 4. Because a portion of the illumination light having entered the objective optical system 4 is directed to the image capturing element 5 by Fresnel reflection at the distal end face of the objective optical system 4, by reducing the illumination light itself entering the objective optical system 4, the flare prevention effect can be improved.

When this inclined surface 10a is provided, it is desirable that the inclination angle θ of the inclined surface 8a of the through-hole 8 with respect to the distal end face of the objective optical system 4 satisfy Conditional Expression (2) below:

$$no/ni \leq \cos\theta \quad (2)$$

where no is the refractive index of the material in contact with the inclined surface 8a, such as the objective optical system 4 or a filler.

Figure 9:
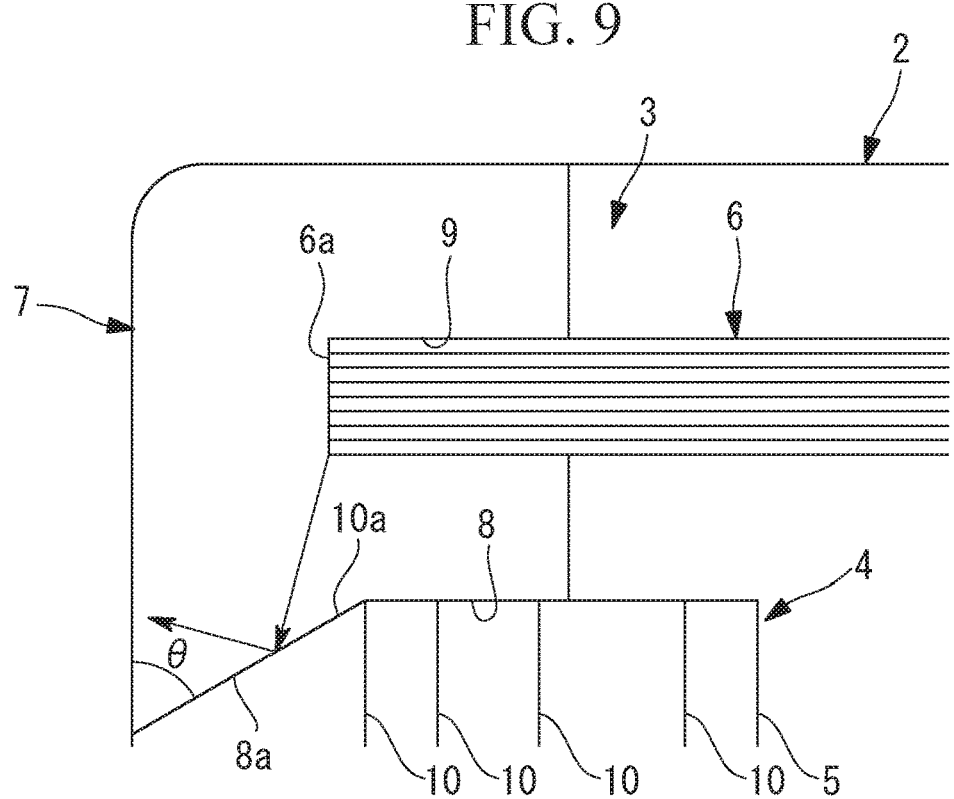
FIG. 9 is a diagram for explaining Conditional Expression (1) in the endoscope in FIG. 5.

By satisfying Conditional Expression (2), even when illumination light is incident on the inclined surface 8a from a direction substantially perpendicular to the optical axis, it is possible to totally reflect the illumination light at the inclined surface 8a, as shown in FIG. 9, and thus to improve the flare prevention effect.

Table 2 shows example material combinations and maximum inclination angles satisfying Conditional Expression (2).

TABLE 2

| SUBSTANCE IN CONTACT WITH INNER SURFACE OF THROUGH-HOLE | RESIN LAYER P1 | RESIN LAYER P2 | GLASS | AIR | ADHESIVE |
|---|---|---|---|---|---|
| no | 1.546 | 1.532 | 1.497 | 1 | 1.505 |
| TRANSPARENT DISTAL-END ELEMENT | | | POLYSULFONE | | |
| ni | | | 1.635 | | |
| no/ni | 0.95 | 0.94 | 0.92 | 0.61 | 0.92 |
| (MAXIMUM) INCLINATION ANGLE θ | 19° | 20° | 24° | 52° | 23° |

Figure 10:
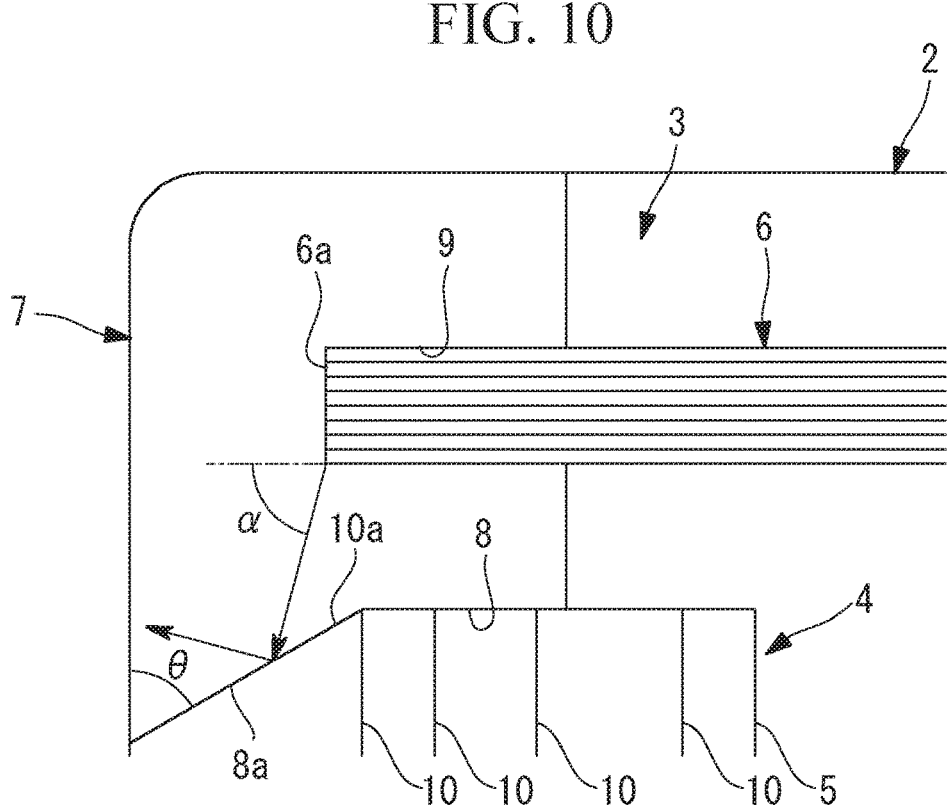
FIG. 10 is a diagram for explaining Conditional Expression (2) in the endoscope in FIG. 5.

The inclination angle θ of the inclined surface 8a may satisfy Conditional Expression (3) below:

$$30° \leq \theta \leq 180° - \alpha - (\sin^{-1}(no/ni)) \quad (3)$$

where α is the angle formed between the illumination light emitted from the exit end 6a of the light guide fiber 6 and the optical axis of the objective optical system 4, as shown in FIG. 10.

By satisfying Conditional Expression (3), it is possible to reduce the outside diameter of the endoscope 1 and to obtain a sufficient flare prevention effect.

More specifically, if θ is reduced, the dimension of the objective optical system 4 in the direction perpendicular to the optical axis needs to be increased, otherwise the distal end face becomes small and the effective diameter cannot be ensured. Hence, the outside diameter of the endoscope 1 is increased. On the other hand, if θ is increased, the amount of illumination light totally reflected at the inclined surface 8a is reduced, and thus, the flare prevention effect is reduced. By satisfying Conditional Expression (3), these inconveniences can be suppressed.

Table 3 shows example material combinations and maximum inclination angles satisfying Conditional Expression (3).

element configured to hold the exit end of the light guide fiber and made of a transparent material that allows the illumination light emitted from the exit end to pass therethrough; and an objective optical system inserted through a through-hole provided in the transparent distal-end element. The refractive index of the transparent material constituting the transparent distal-end element is larger than the refractive index of at least one material in contact with the inner surface of the through-hole.

According to this aspect, the illumination light emitted from the exit end of the light guide fiber enters the transparent distal-end element holding the exit end, passes through the transparent distal-end element, exits from the distal end face of the transparent distal-end element to the outside, and illuminates a site to be observed. A portion of the illumination light emitted from an exit face of the transparent distal-end element at angle to the optical axis or a portion of the illumination light leaking from the side surface of the light guide fiber advances through the transparent distal-end element toward the objective optical system disposed in the through-hole. Because the refractive index of the transparent material constituting the transparent distal-end element is larger than the refractive index of at least one material in contact with the inner surface of the through-hole, a portion of the illumination light is totally reflected at the boundary between the through-hole and the material in contact with the inner surface of the through-hole, and a portion is refracted in a direction further toward the distal end.

Hence, even without a frame partitioning, in the direction perpendicular to the optical axis, the objective optical system and the transparent distal-end element provided there-

TABLE 3

| SUBSTANCE IN CONTACT WITH INNER SURFACE OF THROUGH-HOLE | RESIN LAYER P1 | RESIN LAYER P2 | GLASS | AIR | ADHESIVE |
|---|---|---|---|---|---|
| no | 1.546 | 1.532 | 1.497 | 1 | 1.505 |
| TRANSPARENT DISTAL-END ELEMENT | | | POLYSULFONE | | |
| ni | | | 1.635 | | |
| no/ni | 0.95 | 0.94 | 0.92 | 0.61 | 0.92 |
| LIGHT DISTRIBUTION ANGLE | 60° | 120° | 90° | 140° | 110° |
| α | 30° | 60° | 45° | 70° | 55° |
| (MAXIMUM) INCLINATION ANGLE θ | 79° | 50° | 69° | 72° | 58° |

As a result, the above-described embodiment also leads to the following aspect.

An aspect of the present invention provides an endoscope including: a light guide fiber having an exit end through which illumination light is emitted; a transparent distal-end around, it is possible to reduce the illumination light entering the objective optical system and directed toward the base end in the optical axis direction, and thus to prevent the occurrence of flare. It is also possible to reduce the outside diameter of the endoscope and to reduce the cost.

In the above aspect, the objective optical system may include a plurality of resin layers laminated in the optical axis direction, and the outer peripheral surfaces of the resin layers may be in contact with the inner surface of the through-hole.

With this configuration, by using a reasonable objective optical system formed by laminating resin layers, the cost can be further reduced. In addition, simply by selecting materials having smaller refractive indices than the transparent material constituting the transparent distal-end element as the materials of the plurality of resin layers, the cost and the flare can be reduced.

In the above aspect, a filler may be charged between the outer peripheral surface of the objective optical system and the inner surface of the through-hole, and the refractive index of the filler may be smaller than the refractive index of the transparent material constituting the transparent distal-end element.

With this configuration, by filling the gap between the objective optical system and the transparent distal-end element with a filler, the objective optical system is more reliably supported by the transparent distal-end element. Hence, even if the frame is eliminated to reduce the outside diameter of the endoscope and to reduce the cost, the occurrence of flare can be suppressed by utilizing the refractive index difference between the transparent distal-end element and the filler.

In the above aspect, the filler may be an adhesive.

With this configuration, by filling the gap between the objective optical system and the transparent distal-end element with a filler made of an adhesive, the objective optical system is more reliably fixed by the transparent distal-end element. Hence, even if the frame is eliminated to reduce the outside diameter of the endoscope and to reduce the cost, the occurrence of flare can be suppressed by utilizing the refractive index difference between the transparent distal-end element and the filler.

In the above aspect, the outer peripheral surface at the distal end portion of the objective optical system and the inner surface at the distal end portion of the through-hole in the transparent distal-end element may have inclined surfaces that are gradually tapered toward the distal ends.

With this configuration, the angle of incidence of the illumination light on the boundary between the through-hole and the material in contact with the inner surface of the through-hole can be further increased at the portion where the inclined surfaces are provided, which makes it easy to satisfy the total reflection condition. As a result, it is possible to reduce the amount of illumination light passing through the boundary and thus to further suppress the occurrence of flare.

In the above aspect, the angle of the inclined surface in the transparent distal-end element with respect to the distal end face of the objective optical system may satisfy the Conditional Expression below:

$$no/ni \leq \cos\theta$$

where no is the refractive index of the material in contact with the inner surface of the through-hole, ni is the refractive index of the transparent material constituting the transparent distal-end element, and θ is the angle of the inclined surface in the transparent distal-end element with respect to the distal end face of the objective optical system.

With this configuration, even when the illumination light is incident on the inclined surface of the transparent distal-end element from the direction perpendicular to the optical axis, the illumination light is totally reflected. Thus, it is possible to increase the flare prevention effect.

In the above aspect, the angle of the inclined surface in the transparent distal-end element with respect to the distal end face of the objective optical system may satisfy the Conditional Expression below:

$$30° \leq \theta \leq 180° - \alpha - (\sin^{-1}(no/ni))$$

where α is the angle formed between the illumination light emitted from the exit end and the optical axis direction.

If θ is too small, the dimension of the objective optical system in the direction perpendicular to the optical axis needs to be increased to ensure the effective diameter of the objective optical system, which leads to an inconvenience that the outside diameter of the endoscope increases. If θ is too large, the flare prevention effect decreases. By satisfying the above-described condition, it is possible improve the flare prevention effect while reducing the outside diameter of the endoscope.

In the above aspect, the refractive indices of the plurality of resin layers may increase toward the distal end.

With this configuration, the illumination light having entered the objective optical system is prevented from totally reflected at boundaries between the resin layers when obliquely traveling from the image-plane side toward the object-plane side, and the angle of incidence thereof on each resin-layer boundary sequentially decreases. Hence, the illumination light is less likely to reach the image capturing face, and thus it is possible to improve the flare prevention effect.

The present invention provides an advantage in that it is possible to prevent the occurrence of flare while reducing the outside diameter of the endoscope and reducing the cost by eliminating a frame that blocks light between the objective optical system and the transparent distal-end element.

REFERENCE SIGNS LIST 1 endoscope
4 objective optical system
6 light guide fiber
6a exit end
7 transparent distal-end element
8 through-hole
8a, 10a inclined surface
10 resin layer
ni, no refractive index

The invention claimed is:
1. An endoscope comprising:
a light guide fiber having an exit end through which illumination light is emitted;
a transparent distal-end element configured to hold the exit end of the light guide fiber and made of a transparent material that allows the illumination light emitted from the exit end to pass therethrough; and
an objective optical system inserted through a through-hole provided in the transparent distal-end element,
wherein at least a portion of the illumination light enters the objective optical system through a boundary between the transparent distal-end element and the objective optical system, and
a refractive index of the transparent material constituting the transparent distal-end element is larger than a refractive index of at least one material in contact with an inner surface of the through-hole.

2. The endoscope according to claim 1, wherein
the objective optical system comprises a plurality of resin layers laminated in an optical axis direction, and
outer peripheral surfaces of the plurality of resin layers are in contact with the inner surface of the through-hole.

3. The endoscope according to claim 1, wherein
a filler is charged between an outer peripheral surface of the objective optical system and the inner surface of the through-hole, and
the refractive index of the filler is smaller than the refractive index of the transparent material constituting the transparent distal-end element.

4. The endoscope according to claim 3, wherein the filler comprises an adhesive.

5. The endoscope according to claim 1, wherein an outer peripheral surface at a distal end portion of the objective optical system and the inner surface at a distal end portion of the through-hole in the transparent distal-end element have inclined surfaces that are gradually tapered toward distal ends thereof.

6. The endoscope according to claim 5, wherein an angle of the inclined surface in the transparent distal-end element with respect to a distal end face of the objective optical system satisfies a conditional expression below:

$$no/ni \leq \cos\theta$$

where no is the refractive index of the material in contact with the inner surface of the through-hole, ni is the refractive index of the transparent material constituting the transparent distal-end element, and $\theta$ is the angle of the inclined surface in the transparent distal-end element with respect to the distal end face of the objective optical system.

7. The endoscope according to claim 6, wherein the angle of the inclined surface in the transparent distal-end element with respect to the distal end face of the objective optical system satisfies a conditional expression below:

$$30° \leq \theta \leq 180° - \alpha - (\sin^{-1}(no/ni))$$

where $\alpha$ is the angle formed between the illumination light emitted from the exit end and an optical axis direction.

8. The endoscope according to claim 2, wherein the refractive indices of the plurality of resin layers increase toward a distal end.

9. An endoscope comprising:
a light guide fiber having an exit end through which illumination light is emitted;
a transparent distal-end element configured to hold the exit end of the light guide fiber and made of a transparent material that allows the illumination light emitted from the exit end to pass therethrough; and
an objective optical system inserted through a through-hole provided in the transparent distal-end element,
wherein a refractive index of the transparent material constituting the transparent distal-end element is larger than a refractive index of at least one material in contact with an inner surface of the through-hole, and
an outer peripheral surface at a distal end portion of the objective optical system and an inner surface at the distal end portion of the through-hole in the transparent distal-end element have inclined surfaces that are gradually tapered toward distal ends thereof.

10. The endoscope according to claim 9, wherein
the objective optical system includes a plurality of resin layers laminated in an optical axis direction, and
outer peripheral surfaces of the plurality of resin layers are in contact with the inner surface of the through-hole.

11. The endoscope according to claim 9 wherein
a filler is charged between the outer peripheral surface of the objective optical system and the inner surface of the through-hole, and
a refractive index of the filler is smaller than the refractive index of the transparent material.

12. The endoscope according to claim 11, wherein the filler comprises an adhesive.

13. The endoscope according to claim 9, wherein an angle of the inclined surface in the transparent distal-end element with respect to a distal end face of the objective optical system satisfies a conditional expression below:

$$no/ni \leq \cos\theta$$

where no is the refractive index of the material in contact with the inner surface of the through-hole, ni is the refractive index of the transparent material constituting the transparent distal-end element, and $\theta$ is the angle of the inclined surface in the transparent distal-end element with respect to the distal end face of the objective optical system.

14. The endoscope according to claim 13, wherein the angle of the inclined surface in the transparent distal-end element with respect to the distal end face of the objective optical system satisfies a conditional expression below:

$$30° \leq \theta \leq 180° - \alpha - (\sin^{-1}(no/ni))$$

where $\alpha$ is the angle formed between the illumination light emitted from the exit end and an optical axis direction.

15. An endoscope comprising:
a light guide fiber having an exit end through which illumination light is emitted;
a transparent distal-end element configured to hold the exit end of the light guide fiber and made of a transparent material that allows the illumination light emitted from the exit end to pass therethrough; and
an objective optical system inserted through a through-hole provided in the transparent distal-end element,
wherein a refractive index of the transparent material constituting the transparent distal-end element is larger than a refractive index of at least one material in contact with an inner surface of the through-hole,
the objective optical system includes a plurality of resin layers laminated in an optical axis direction,
outer peripheral surfaces of the plurality of resin layers are in contact with the inner surface of the through-hole, and
the refractive indices of the plurality of resin layers increase toward a distal end.

16. The endoscope according to claim 15, wherein
a filler is charged between an outer peripheral surface of the objective optical system and the inner surface of the through-hole, and
a refractive index of the filler is smaller than the refractive index of the transparent material.

17. The endoscope according to claim 16, wherein the filler comprises an adhesive.

\* \* \* \* \*